United States Patent
Weder et al.

(10) Patent No.: US 10,481,323 B2
(45) Date of Patent: Nov. 19, 2019

(54) PHYSIOLOGICALLY RESPONSIVE MECHANICALLY ADAPTIVE POLYMER OPTICAL FIBERS, PRODUCTION AND METHODS OF USE (71) Applicant: ADOLPHE MERKLE INSTITUTE, UNIVERSITY OF FRIBOURG, Fribourg (CH)

(72) Inventors: Christoph Weder, Düdingen (CH); Mehdi Jorfi, Fribourg (CH); E. Johan Foster, Fribourg (CH)

(73) Assignee: ADOLPHE MERKLE INSTITUTE, UNIVERSITY OF FRIBOURG, Fribourg (CH)

(*) Notice: Subject to any disclaimer, the term of this patent is extended or adjusted under 35 U.S.C. 154(b) by 684 days.

(21) Appl. No.: 15/112,580

(22) PCT Filed: Feb. 13, 2015

(86) PCT No.: PCT/EP2015/053140
§ 371 (c)(1),
(2) Date: Jul. 19, 2016

(87) PCT Pub. No.: WO2015/121437
PCT Pub. Date: Aug. 20, 2015

(65) Prior Publication Data
US 2016/0334571 A1 Nov. 17, 2016

Related U.S. Application Data

(60) Provisional application No. 61/939,893, filed on Feb. 14, 2014.

(51) Int. Cl.
G02B 6/02 (2006.01)
A61N 5/06 (2006.01)

(52) U.S. Cl.
CPC ....... *G02B 6/02033* (2013.01); *A61N 5/0601* (2013.01); *A61N 5/0622* (2013.01);
CPC ........... *A61N 2005/063* (2013.01); *A61N 2005/0612* (2013.01); *A61N 2005/0659* (2013.01); *A61N 2005/0662* (2013.01)

(58) Field of Classification Search
CPC combination set(s) only.
See application file for complete search history.

(56) References Cited

U.S. PATENT DOCUMENTS

| | | | | |
|---|---|---|---|---|
| 2001/0026666 | A1* | 10/2001 | Ferrera | G02B 6/403 385/123 |
| 2007/0003200 | A1* | 1/2007 | Collaro | C03B 37/0253 385/127 |
| 2010/0241100 | A1* | 9/2010 | Blumenfeld | A61B 5/0075 604/503 |

FOREIGN PATENT DOCUMENTS

| | | |
|---|---|---|
| GB | 1277496 A | 6/1972 |
| WO | WO9932918 A1 | 7/1999 |

* cited by examiner

*Primary Examiner* — Scott Luan
(74) *Attorney, Agent, or Firm* — Hudak, Shunk & Farine Co. LPA (57) ABSTRACT

Physiologically responsive mechanically adaptive optical fibers that are suitable for optical interfacing with living organisms. The optical fibers are particularly suited for applications in optogenetics. Dry, stiff fibers display a desirable tensile storage modulus and can be readily inserted into biological and in particular cortical tissue. Exposure to conditions encountered in vivo results in reduction, often a drastic reduction in modulus. When coupled with a suitable light source, the construction can be utilized to stimulate neurons in vivo. Methods for producing and utilizing the optical fibers and devices including the optical fibers are disclosed.

18 Claims, 6 Drawing Sheets

PHYSIOLOGICALLY RESPONSIVE MECHANICALLY ADAPTIVE POLYMER OPTICAL FIBERS, PRODUCTION AND METHODS OF USE

FIELD OF THE INVENTION

The present invention relates to physiologically responsive mechanically adaptive optical fibers that are suitable for optical interfacing with living organisms, and are particularly suited for applications in optogenetics. Dry, stiff fibers display a desirable tensile storage modulus and can be readily inserted into biological and in particular cortical tissue. Exposure to water or conditions encountered in vivo results in reduction, often a drastic reduction, in modulus. When coupled with a suitable light source, the construction can be utilized to stimulate neurons in vivo. Methods for producing and utilizing the optical fibers and devices including the optical fibers are disclosed.

BACKGROUND OF THE INVENTION

Neural interfaces, which (re)connect the brain with the outside world, are enabling tools for studies of the brain function and also essential elements for a broad range of clinical applications. While intracortical microelectrodes, which can electrically record or stimulate the activity of individual or small populations of neurons, have been known for decades, the discovery that optical signals can be used to interface with neurons is a more recent development. In particular the possibility to activate or mute neurons using photosensitive proteins has opened up new possibilities in the field of neural interfacing. Optogenetic technology is thus generating considerable excitement in neuroscience and biomedical engineering, and has quickly become a widely used toolbox to investigate the brain function and behavior in a broad variety of organisms that ranges from zebrafish to rodents to nonhuman primates.

The majority of optogenetics studies conducted in vivo use optical fibers, which are sometimes guided through an implanted cannula and/or combined with a tungsten microelectrode. In a recent study, Zorzos et al. extended the design concept to three-dimensional microwaveguides, which are capable of delivering light to targets distributed in a 3D pattern throughout the brain. While such optical interfaces have successfully been used in many short-term animal experiments, long-term in vivo studies are only emerging. The possibility to use optogenetic tools under chronic conditions, ideally in freely moving animals and with minimal neuroinflammatory response, is desirable for both fundamental studies and possible clinical applications, but reliable chronic interfaces have proved difficult to realize. A growing body of work gathered in connection with electrophysiological implants suggests that the mechanical mismatch of rigid neural implants and the much softer cortical tissue is a contributing factor to the cell-mediated inflammatory responses, neuronal dieback, and eventual encapsulation of cortical implants. We speculate that the mechanical mismatch of conventional optical fibers and the cortical tissue may cause similar effects in chronic optogenetic applications. One recent approach to alleviate the problems arising from such mechanical mismatch between neural microelectrodes and the cortical tissue is the development of physiologically responsive mechanically adaptive materials, which are sufficiently rigid to permit insertion of small-diameter implants, but which soften considerably upon exposure to emulated physiological conditions. Such adaptive materials can be made by creating nanocomposites consisting of polymers and rigid nanofillers, in which the interactions between the nanofiller particles, and therewith the overall mechanical properties, can be influenced by exposure to water. For example, the tensile storage modulus (B) of nanocomposites based on poly(vinyl alcohol) and cellulose nanocrystals is reduced from ~14 GPa in the dry state at room temperature to ~10 MPa upon exposure to simulated physiological conditions. We present here new physiologically responsive mechanically adaptive optical fibers that are useful for optogenetic and other in-vivo applications, because they may reduce inflammatory responses and have other attractive features. For example, they can be bent to adapt desirable shape. No optical fibers that satisfy all of the conditions required are known.

For example, since the introduction of nanocellulose into polymers is normally accompanied by increased light scattering, the aforementioned mechanically adaptive nanocomposites are not well suited as basis for adaptive optical fibers and alternative design approaches are needed.

In view of the above, one problem which the present invention has solved is to develop optical fibers and devices including the same that produce a relatively low neural inflammatory response, wherein the devices can be utilized to stimulate neurons in vivo.

Yet another problem which the present invention has solved is to provide physiologically responsive mechanically adaptive polymer optical fibers exhibiting adequate optical properties, in particular relatively low optical losses.

Still another problem which the invention has solved is to provide optical fibers which have a sufficient rigidity to permit insertion into biological and in particular cortical tissue yet soften to a desired degree upon exposure to conditions encountered in vivo.

SUMMARY OF THE INVENTION

The problems noted above and others are solved by the physiologically responsive mechanically adaptive polymer optical fibers of the present invention and stimulation devices incorporating the same.

Accordingly, an object of the present invention to provide optical fibers that have an initial stiffness that allows insertion into biological tissue, and in particular cortical tissue, wherein the optical fibers soften upon exposure to conditions encountered in vivo.

It is a further object of the present invention to provide optical fibers comprising or consisting of largely amorphous polymers having a glass transition temperature above room temperature or about 21° C., with the polymers having the ability to soften upon exposure to conditions encountered in vivo because they swell when contacted with water or body fluid whereby the glass transition temperature is lowered.

Still another object of the present invention is to provide a method for producing optical fibers including the steps of wet-spinning and subsequent crosslinking of the polymer by annealing or an alternative crosslinking process.

An additional object of the present invention is to provide a method for producing optical fibers including the steps of wet spinning fibers; coagulating the spun fibers in a non-solvent; optionally aligning the fibers; and annealing the fibers or crosslinking them with an alternative process.

A further object of the present invention is to provide a neuron stimulation device and methods for producing the same, wherein the device includes physiologically responsive mechanically adaptive optical fibers operatively connected to a light source, for example a light-emitting diode.

In one embodiment of the present invention, a physiologically responsive mechanically adaptive optical fiber is disclosed, comprising a largely amorphous polymer, the fiber having a length, wherein light can be transmitted along the length of the fiber, wherein the fiber has a first stiffness before exposure to conditions encountered in vivo, and upon exposure to conditions encountered in vivo the fiber, over its entire length or a portion thereof, exhibits a second stiffness lower than the first stiffness and is still able to transmit light.

In another embodiment of the present invention, a method for producing an optical fiber is disclosed, comprising the steps of obtaining a solution comprising a largely amorphous polymer, spinning a fiber from the solution into a coagulation bath comprising a coagulant, removing the fiber from the bath; optionally orienting the fiber, crosslinking the polymer and/or annealing the fiber to produce the optical fiber.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

As indicated herein, the invention relates to the design, fabrication and use of physiologically responsive mechanically adaptive optical fibers made from amorphous polymer that can be used as optogenetic stimulants. The optical fibers of the invention have an initial stiffness, which permits facile insertion of small-diameter implants into biological tissue and in particular cortical tissue. Upon exposure to conditions encountered in vivo, which for the purpose of this invention should mean biological fluids, human or animal tissue, or emulated physiological conditions (aqueous solutions with a temperature of 35-40° C.) the stiffness of the fibers is reduced, for example up to 200-fold in one embodiment, while the concomitant changes to the fibers optical properties are small. In one embodiment of the present invention, this softening occurs on account of swelling of an originally dry fiber with (part of the) aqueous biological fluid, which causes plasticization. The optical fibers can deliver light in a range of wavelengths that is sufficiently intense to stimulate neurons in the brain. Stimulation devices comprising optical fibers coupled with a light source, for example a light-emitting diode, are provided. Even without a low-refractive index cladding, which is optional, the physiologically responsive mechanically adaptive optical fibers disclosed herein are useful tools for use in optogenetic studies and applications.

The optical fibers of the present invention include a main body generally having a length, defined by a first end and a second end, and preferably a diameter; maximum that comprises or consists of a largely amorphous polymer. As it is well known to those skilled in the art, the crystallites in semicrystalline polymers cause light scattering and the extent of light scattering often increases with increasing degree of crystallinity. Therefore, preferred embodiments of the present inventions involve polymers which have low crystallinity or which are completely amorphous; such polymers are herein referred to as largely amorphous. For the purpose of this invention, the term "largely amorphous" should serve to describe polymers with a crystallinity of less than 50%, preferably less than 30% and most preferably less than 10%.

To achieve a high stiffness in the initial ex-vivo state, the largely amorphous polymer has in its dry state a glass transition temperature above room temperature, which for the purpose of this application is defined as about 21° C. In one embodiment of the present invention, it has the ability to swell when contacted with water, animal or human tissue or a physiological fluid to the extent that upon swelling the glass transition temperature of the polymer is lower than the initial glass transition temperature, preferably lower than human or animal body temperature, and most preferably lower than room temperature. As the glass transition temperature is lowered from above to below the usage temperature upon swelling, the stiffness of the fiber is reduced.

The optical fiber according to the present invention should not dissolve upon exposure to conditions encountered in vivo. One way to achieve this is crosslinking of the fibers during or after processing. The crosslinks can be of physical or chemical nature. Chemical crosslinks can be introduced by annealing or reaction with an auxiliary crosslinking agent. The degree of swelling must be sufficiently large to reduce the glass transition temperature from above to below the usage temperature, but excessive swelling may unnecessarily increase the inflammation around the fiber in vivo. It is well known in the art that the degree of aqueous swelling of a water-swellable polymer, and therewith the mechanical properties in the water-swollen state, can usually be controlled via the cross-link density. As an alternative to cross-linking, one can select a polymer that is intrinsically water-insoluble, but swells with water under physiological conditions, such as for example poly(vinyl acetate) or partially hydrolyzed poly(vinyl acetate).

In another embodiment, the largely amorphous polymer has a glass transition temperature above room temperature, which for the purpose of this application is defined as about 21° C., but below the temperature of the biological tissue in which the optical fibers of the present invention are used. As the optical fiber is brought in contact with said tissue, the stiffness of the fiber is reduced.

Examples of suitable polymers include, but are not limited to, polyvinyl alcohol, poly(vinyl acetate) and partially hydrolyzed poly(vinyl acetate), poly(vinylbutyral) and partially hydrolyzed poly(vinylbutyral), poly(acrylate)s and acrylate copolymers, polyesters, poly(acrylic acid), poly(ethylene oxide) and ethylene oxide copolymers, poly(propylene oxide) and propylene oxide copolymers, polyamides, poly(acrylamide)s, poly(N-vinyl pyrrolidone)s, and poly(methacrylic acid). It will be apparent to those skilled in the art that other polymers known to be useful as hydrogels for biomedical applications may be useful in the context of the present invention, if the degree of swelling is reduced by way of adequate means such as cross-linking or copolymerization with monomers that reduce such swelling. Of course, the final embodiment must be substantially biocompatible, i.e. it should not cause any substantial negative effects during the intended usage when implanted into biological tissue and, in particular, cortical tissue.

The largely amorphous polymer may be used in its neat form, or in combination with additives, which include but are not limited to plasticizers or antiplasticizers, stabilizers, processing aids, dyes, chromophores or photoluminescent species.

As mentioned heretofore, it can be desirable or even be essential to cross-link the polymer during or after fabrication of the fibers to avoid full or partial dissolution of the fibers upon contact with water or physiological conditions, and limit the extent of aqueous swelling to a minimum, i.e. to a level where the desired mechanical switching is just achieved as excessive swelling beyond the point where the glass transition temperature is reduced to just below the physiological temperature may not be desirable.

The organic solvent to be mixed with water in this invention should be compatible with water, preferably miscible with water at any mixing ratio. Examples of suitable organic solvents include, but are not limited to, dimethyl sulfoxide, dimethyl formamide, glycerine, ethylene glycol, propylene glycol, and triethylene glycol. Of these organic solvents, dimethyl sulfoxide is the most preferable due to its high solubility for most of largely amorphous polymers and in particular PVA and a desirable dependence of the freezing point depression on the mixing ratio of dimethyl sulfoxide and water.

Examples of the coagulants of the coagulating bath include but are not limited to methanol, and saturated aqueous salt solutions comprising for example sodium sulfate, potassium sulfate, ammonium sulfate, potassium thiocyanate, or calcium acetate.

Poly(vinyl alcohol) (PVA) has been used in a wide variety of biomedical applications including contact lenses and FDA-approved nerve grafts. In recent papers or patents that are hereby incorporated by reference, see Potter, K. A.; Jorfi, M.; Householder, K. T.; Foster, E. J.; Weder, C.; Capadona, J. R.; Curcumin-releasing mechanically adaptive intracortical implants improve proximal neuronal density and blood-brain barrier stability; *Acta Biomaterialia* 2014, 10, 2209-2222, Jorfi, M.; Roberts, M. N.; Foster, E. J.; Weder, C.; Physiologically-Responsive, Mechanically-Adaptive Bio-Nanocomposites for Biomedical Applications; *ACS Appl. Mat. Interf.* 2013, 5, 1517-1526, Weder, C.; Foster, E. J.; Jorfi, M.; Roberts, M. N.; Polymer Nanocomposites Having Switchable mechanical Properties; European Patent Application 61/700,995 filed 2012, we have shown that heat-treatment renders solution-cast PVA films water-insoluble, that the extent of aqueous swelling can be controlled via the conditions of the heat treatment, and that such films show water-induced mechanical switching, on account of plasticization upon minimal swelling. However, PVA is notorious for its tendency to crystallize and crystalline PVA fibers are known to suffer from significant light scattering effects.

Figure 1:
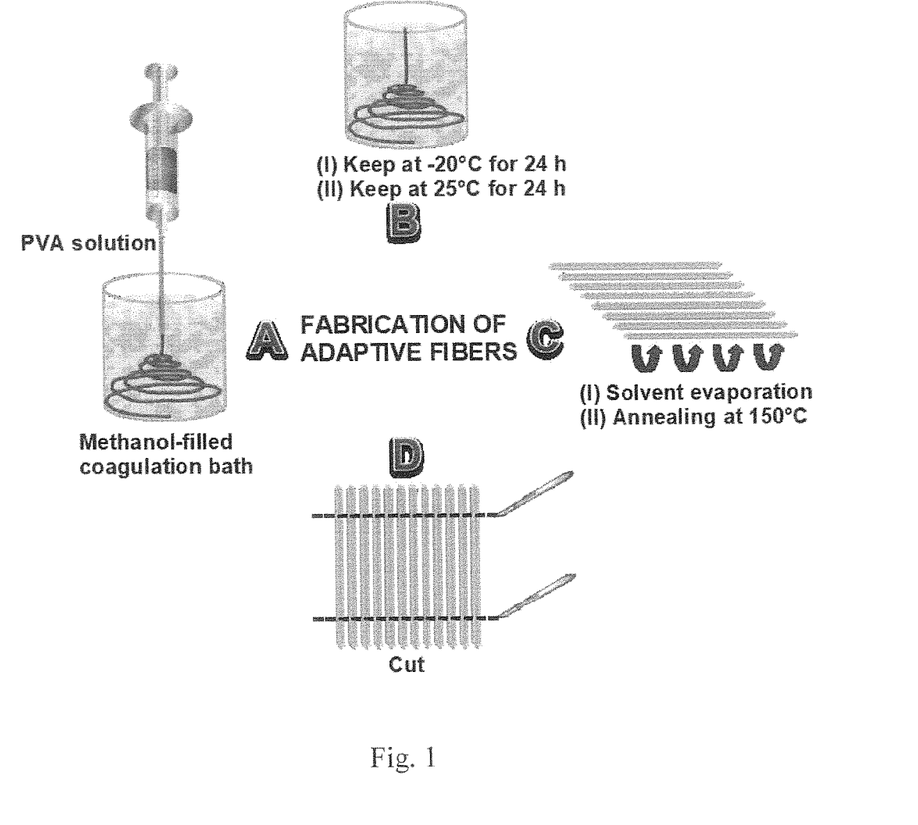
FIG. 1 is a schematic representation of the various processing steps used to fabricate physiologically responsive, mechanically adaptive optical fibers based on poly(vinyl alcohol) (PVA).

We now surprisingly discovered that it is possible to create PVA fibers, which are characterized in that they are water insoluble, physiologically responsive and mechanically adaptive, and have low optical losses that render them suitable for optogenetic studies and applications. According to the present invention this can be achieved by a fabrication process that is schematically illustrated in FIG. 1, and which includes a wet-spinning step, a coagulation step, and an annealing step or other process that crosslinks the fibers after formation. It is noted that other cross-linking chemistries than the one exemplarily employed can be utilized in the here-described process. For example, it is well known that PVA can be cross-linked with difunctional compounds such as diisocyanates (Vadrucci, R.; Weder, C.; Simon, Y. C.; Organogels for Low-Power Light Upconversion; Materials Horizons 2015, 2, 120-124), dianhydrides, diacid chlorides or sodium tetraborate decahydrate.

The wet-spinning step process utilizes a solution of the polymer. In one embodiment, the polymer solution comprises a largely amorphous polymer such as poly(vinyl alcohol) in a concentration of about 2 to about 50 mg/mL and preferably from about 5 to about 20 mg/mL, and most preferably 10 mg/mL. In one embodiment the solution comprises a mixed solvent of water and an organic solvent dimethyl sulfoxide (DMSO) ranges from about 1:9 to about 5:5 v/v and most preferably 2:8 v/v. The polymer solution is spun utilizing a spinneret, for example having a diameter of about 0.5 to about 2.0 mm for example 0.8 mm; and a flow rate of about 0.1 to about 1.0 mL/min, for example 0.36 mg/mL.

The fibers produced by the spinning process are immersed in a coagulation bath comprising the coagulant for a suitable period of time, for example from about 6 to about 48 hours and preferably from about 12 to about 24 hours at a temperature of about −10 to about −25° C. and preferably at about −20° C. Thereafter, the temperature can be raised for example to room temperature or about 21° C. for a further period of time, for example from about 6 to about 48 hrs., and preferably from about 12 to about 24 hrs. In one embodiment the coagulant comprises methanol.

The post-coagulated fibers are then subjected to the annealing step. Optionally, the fibers are fixated in a desired shape during at least a portion of the annealing step, so that the shape imparted through fixation is substantially retained. The annealing step can comprise an initial drying period, for example for a suitable period of time to induce drying of the fibers through evaporation of any remaining solvents and/or the coagulating liquid. In one embodiment initial drying is performed for a period of time from 5 min to about 48 hrs. at a temperature of about 20 to about 60° C., and preferably at about 45 to about 55° C. The optical fibers are then heat-treated at a temperature from about 100 to about 160° C. and preferably from about 140 to about 150° C. for a suitable period of time from about 1 to about 60 minutes in order to render the fibers insoluble in water and physiological liquids.

Figure 2:
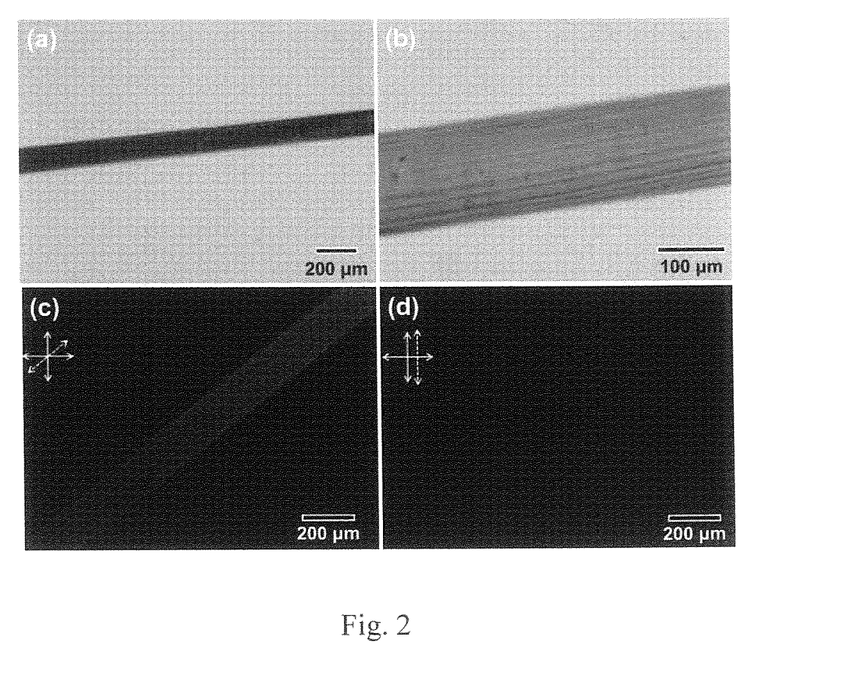
FIG. 2 presents optical microscopic images of a PVA fiber (a, b); cross-polarized optical micrographs of a PVA fiber arranged with its long axis oriented with angles of 45° (c) and 0° (d) relative to the analyzer; the orientation of the polarizers (solid arrows) and sample (dashed arrows) is also shown.

This procedure produces optical fibers having substantially homogeneous cross-sections and smooth surfaces, see the examples set forth in FIG. 2. The optical fibers may possess some degree of uniaxial orientation which is also illustrated in FIG. 2.

As an alternative to the process schematically illustrated in FIG. 1, an auxiliary crosslinking agent such as, but not limited to, glutaraldehyde, sodium metaborate, sodium tetraborate, potassium metaborate, ammonium borate, calcium metaborate, calcium tetraborate, boric acid, a multifunctional isocyanate, a multifunctional acid chloride, sodium tetraborate decahydrate and optionally a catalyst that catalyzes the cross-linking reaction is included in either the spinning solution used in the wet-spinning step or the coagulant used in the coagulation step, or is applied to the fibers after coagulation or after drying. In this case the annealing step may become obsolete or can be modified. Optionally, unreacted cross-linker, catalyst and solvent that may be used to imbibe the fibers with the cross-linker are removed after the cross-linking step.

Optionally, the fibers can be clad with one or more layers of materials that exhibit a lower refractive index than the unclad fiber. The cladding, which must be in intimate contact with the fiber core, is often advantageous because it enhances light confinement to the core of the fiber by total internal reflection at the interface and thereby increases light transmittance through the fiber. Optionally, the fibers can be combined with other functional elements, for example, but not limited to an electrical recording or electrical stimulation device. Similarly, the fibers may be combined with other materials, for example in the form of electrically conducting as well as electrically insulating layers, to achieve such multiple functionality.

Stimulation devices are produced by coupling the optical fiber to a light source. In a preferred embodiment, the wavelength of light is between 254 and 880 nm; in a more preferred embodiment, the wavelength of light is between 365 and 680 nm; in the most preferred embodiment the wavelength of light is between 460 and 600 nm; In a preferred embodiment, the light source is coupled to one end of the fiber. Suitable light sources include, but are not limited to lasers and light emitting diodes having a suitable output in order to delivery light with a power density of greater than 1 mW/cm$^2$ from the distal end, more preferably greater than 50 mW/cm$^2$ and most preferably greater than 500 mW/cm$^2$ from the distal end, which is more than sufficient to stimulate in vivo.

The optical fibers according to the present invention must have an initial stiff state, which permits facile insertion of small-diameter implants into biological tissue and in particular cortical tissue and they must soften upon exposure to conditions encountered in vivo. The initial stiff state is characterized by a first tensile storage modulus, which is preferably greater than 1 GPa, and the soft state after exposure to in vivo conditions characterized by a second tensile storage modulus of less than 500 MPa. Preferably, the stiff state is characterized by a tensile storage modulus of greater than 2 GPa, more preferably greater than 4 GPa, and most preferably greater than 6 GPa. Preferably, the soft state is characterized by a tensile storage modulus of less than 200 MPa, more preferably smaller than 50 MPa, and most preferably smaller than 10 MPa.

The degree of swelling should be just sufficiently large to reduce the glass transition temperature from above to just below the usage temperature, since excessive swelling may cause an increase of inflammation around the fiber in vivo. Preferably the extent of swelling is below 100%. More preferably the extent of swelling is below 60%. Most preferably the extent of swelling is below 45%.

The optical fibers according to the present invention must have low optical losses in order to be able to transport light. Ideally the optical loss should be below 10 dB/cm, preferably below 5 dB/cm, more preferably below 1 dB/cm, and most preferably below 1 dB/cm at the wavelength at which the optical fibers are used.

EXAMPLES

The various steps of a fabrication process employed are schematically shown in FIG. 1. A wet-spinning process was used to spin a 10 mg/mL solution of PVA (99% hydrolyzed, weight-average molecular weight, $M_w$=85000-124000 g/mol, Sigma Aldrich) in a 4:1 v/v DMSO/water mixture into a coagulation bath of methanol cooled to −20° C., using a spinneret with a diameter of 0.8 mm and a flow rate of 0.36 mL/min. The as-spun PVA fibers were kept immersed in the coagulation bath for 24 h at −20° C. and for another 24 h at room temperature. The methanol-swollen fibers were subsequently aligned and fixated on an aluminum sheet, dried for 24 h in an oven at 50° C., and finally heat-treated at 150° C. for 15 min. This method afforded fibers with a diameter of ~150 μm, and a crystallinity of 20-30%. In recent papers that are hereby incorporated by reference, we have shown that heat-treated solution-cast PVA films exhibit a crystallinity of 30-40%. This comparison shows that the process used here results PVA fibers with lower crystallinity than mechanically adaptive materials known in the art. Optical microscopy images show rather homogeneous cross-sections and smooth surfaces (FIG. 2a,b), while polarized optical microscopy images reveal a high degree of uniaxial orientation (FIG. 2c,d). For this initial study no further cladding was used.

The swelling behavior of the PVA fibers was investigated by immersing them in deionized water at physiological temperature of 37° C. for one day. After one day of incubation in water, the degree of swelling was determined by measuring the weight of the fibers pre- and post-swelling as reported before, yielding an equilibrium water uptake of 35±4.5% w/w.

Dynamic mechanical analysis experiments were carried out to determine the tensile storage modulus (E) of the fibers in the dry and wet state. The PVA fibers display an initial tensile storage modulus E' of 7100±230 MPa (dry state at 25° C., FIG. 3), which is reduced as the temperature is increased above the $T_g$ (~68° C.) to reach a rubbery plateau with an E' of 1630±400 MPa at 100° C. (data not shown, N=3). Upon immersion in water for 1 day at 37° C., the PVA fibers softened substantially to reach an E' of ~35 MPa after equilibration.

Figure 3:
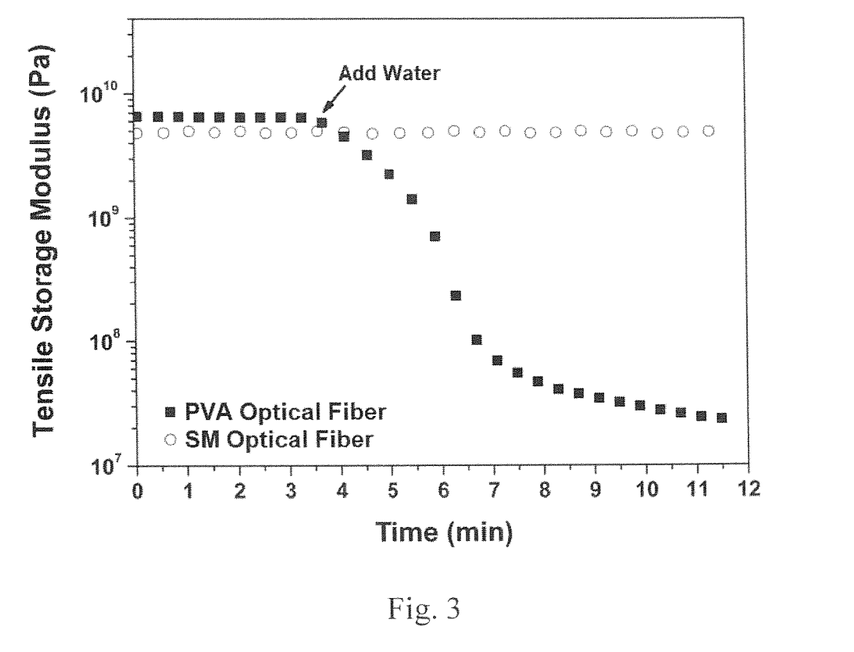
FIG. 3 is a graph showing tensile storage modulus (E) of an adaptive PVA fiber and a commercial single mode (SM) optical fiber (5405-XP, ThorLabs) as a function of immersion time in water at 37° C. The water was added after 3.5 min, as indicated in the figure.

FIG. 3 shows time-dependent measurements of the tensile storage modulus E of a PVA fiber and a SM optical fiber which is a silica core coated with dual acrylate (S405-XP, ThorLabs) as reference, starting in the dry state at room temperature and upon addition of water at 37° C. In the case of the PVA fiber, a rapid (4 min) decrease of E is observed, while the mechanical properties of the conventional SM optical fiber remain unchanged. Thus, mechanical tests confirm unequivocally that the PVA fibers of the present invention here are rigid when dry, but soften considerably upon swelling in water.

Figure 4:
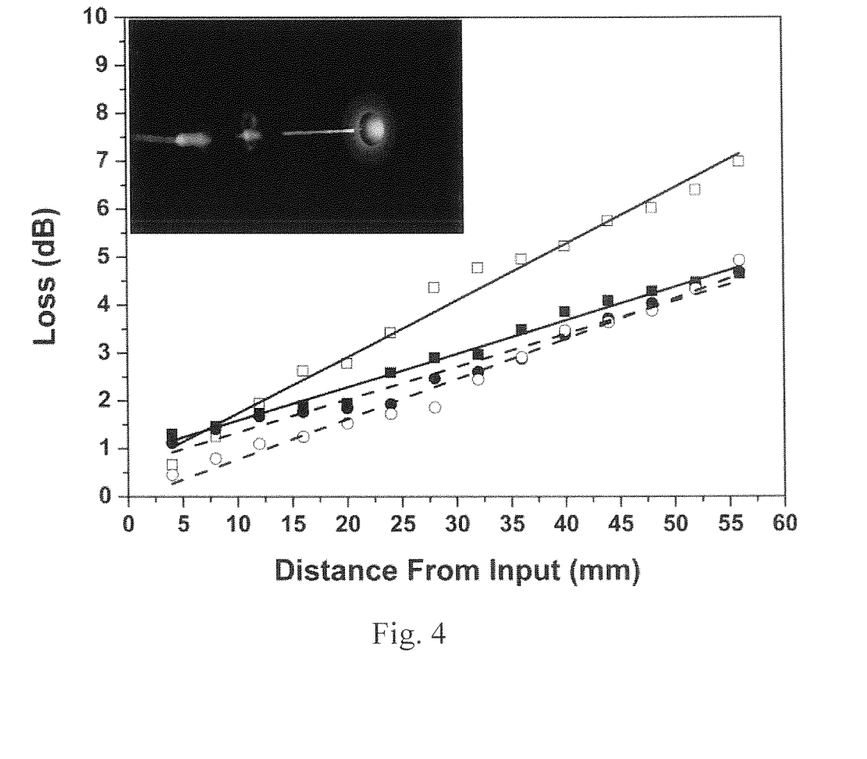
FIG. 4 is a graph showing optical losses of PVA optical fibers in the dry and wet state as function of fiber length. Data are shown for 470 nm (dry, ■; wet, □) and 590 nm (dry, ●; wet, ○) incident light and represent of N=5 samples±standard deviation. Solid (470 nm) and dashed (590 nm) lines are least square fits. The inset shows a photograph of a fiber transmitting 590 nm light in the dry, rigid state.

Blue (470 nm, M470F1, 10.1 mW, ThorLabs) and amber (590 nm, M590F1, 3.2 mW, ThorLabs) fiber-coupled high-power LEDs were used to demonstrate the PVA fibers' ability to deliver light of different wavelengths as they are commonly used in optogenetic applications. The light transmission of the PVA fibers was quantified by determining the loss of light using a cutback method known in the art, in which the optical fibers were truncated and the intensity of the transmitted light was measured using a photodiode (S120VC, ThorLabs) coupled with a photometer (PM100USB, ThorLabs). FIG. 4 shows the light loss as function of fiber length, wavelength, and mechanical state. The propagation losses determined through linear regression of the data sets are 0.7±0.04 dB/cm at 470 nm and 0.6±0.1 dB/cm at 590 nm (N=5) in the dry state.

Figure 5:
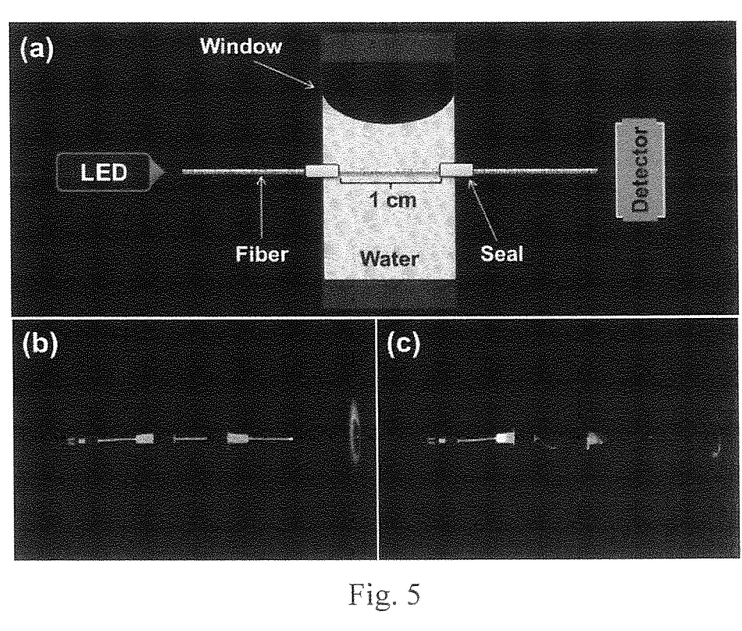
FIG. 5 presents a (a) schematic representation of the cell used to operate optical fibers in the dry rigid and water-swollen soft state, and (b, c) photographs of a 10 cm long PVA fiber transmitting 470 nm light in the dry, rigid state (b) and after adding water of a temperature of 25° C. (c).
Figure 6:
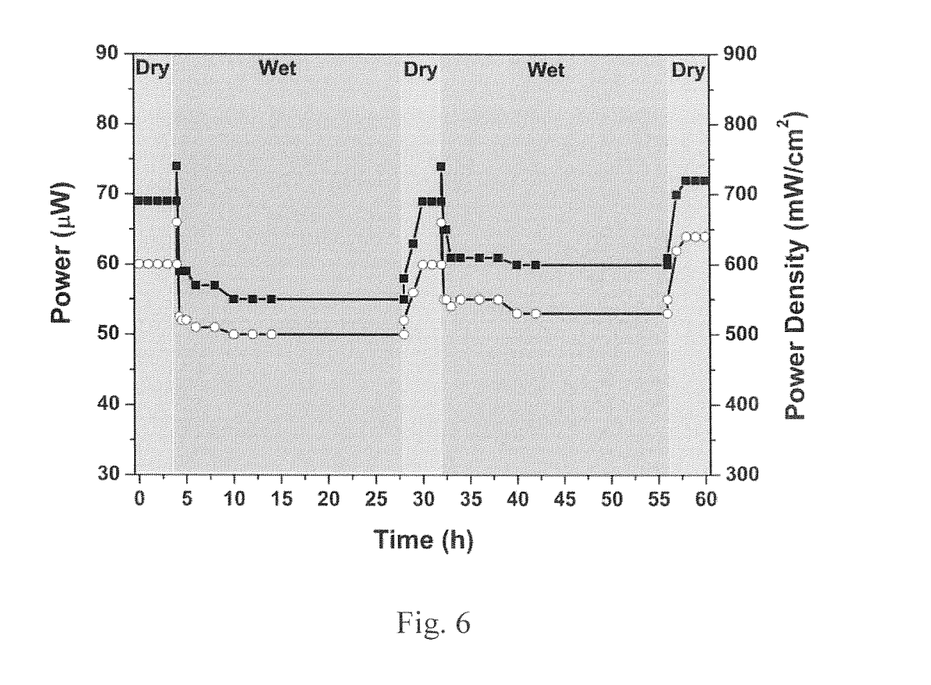
FIG. 6 is a graph showing changes of transmitted power (■) and power density (○) over time as a 10 cm long PVA fiber transporting 470 nm light from a 10.1 mW fiber-coupled high-power LED is switched from the dry, rigid state to the water-swollen soft state (room temperature) and back.

The setup sketched in FIG. 5a was used to measure the optical transmission through the fibers in the rigid dry and wet soft state. The fiber was threaded through two ferrules embedded in opposite windows of a 1 cm×1 cm×5 cm polystyrene cuvette such that the two fiber extremities remained dry while the middle portion could be exposed to a fluid. Light from a 470 nm LED with an output of 10.1 mW was coupled into one end of the fiber. FIGS. 5b and 5c, which show the setup in the dry and water-filled state, reveal no qualitative differences in light transmission and scattering. However, in the water-swollen state the PVA fiber can be readily bent (FIG. 5c). FIG. 6 shows how the transmitted power and power density change over time as the fiber is repeatedly softened by addition of deionized water, and rigidified upon drying. In a first 5 h dry phase, light transmission is stable as expected. Upon addition of water (refractive index n=1.33) a brief increase of the transmitted power (density) of ~10% is observed, which is likely related to the lower scattering loss at the water/fiber interface due to the lower refractive index difference. Upon swelling/softening, the transmission is rapidly decreased by ~15%, which corresponds to the difference of loss between the rigid and soft state at 470 nm for the propagation of the wet portion of the fiber. We speculate that the reduction of the fibers' refractive index on account of swelling with water (n=1.33) and reduced numerical aperture contribute to these relatively small losses; a similar trend was observed by Dupuis et al. for microstructured polymer optical fibers made form cellulose butyrate. FIG. 6 shows that drying and another wetting and drying cycle permitted to reversibly switch the transmission characteristics of the PVA fibers and that under unchanged conditions the transmission stabilized quickly and was then stable for many hours. The propagation loss of the PVA fibers in the water-swollen soft state, measured after immersion for 30 min in water at room temperature, was 1.1±0.1 dB/cm at 470 nm and 0.9±0.3 dB/cm at 590 nm (FIG. 4, N=5), i.e., slightly higher than in the dry state. The linear loss vs. distance functions confirms that the optical properties are homogeneous along the PVA fiber and that smooth bents introduce negligible losses. Due to significant scattering losses imparted by the slightly crystalline polymer, the optical losses of the current PVA fibers are higher than in conventional optical fibers, but their optical properties are clearly sufficient (vide infra) for the targeted application.

The illumination power density required for optogenetic applications is typically in the range of 10-1000 mW/cm². The data in FIG. 6 show that this level can be met with the current PVA fibers. For example, if a LED with an output of 10.1 mW is used, a 150 µm diameter, 10 cm long PVA fiber had an output power density of ~700 and ~500 mW/cm² in the dry and wet state, respectively. Thus, the illumination power achievable with the physiologically responsive, mechanically adaptive PVA fibers described here is adequate to activate neurons in the brain.

In summary, we have demonstrated the design and fabrication of physiologically responsive, mechanically adaptive optical fibers from poly(vinyl alcohol). These fibers offer an initial stiffness of ~7 GPa, which is slightly higher than those of commercial SM optical fibers and permits facile insertion of small-diameter implants into the cortex. Upon exposure to water the fibers swell slightly and their stiffness is reduced 200-fold, while the concomitant changes to the fiber's optical properties are small. We have shown that the optical characteristics of the PVA fibers produced here are already sufficient to meet the demands of this application, and permit to deliver light of a range of wavelengths that is sufficiently intense to stimulate neurons in the brain. The hitherto unavailable mechanical morphing feature of the PVA optical fibers is useful for chronic optogenetics technology.

The invention further relates to the following:

1. A physiologically responsive mechanically adaptive optical fiber, comprising: a largely amorphous polymer, the fiber having a length, wherein light can be transmitted along the length of the fiber, wherein the fiber has a first stiffness before exposure to conditions encountered in vivo, and upon exposure to conditions encountered in vivo the fiber exhibits a second stiffness lower than the first stiffness.

2. The optical fiber according to 1, wherein the polymer has a glass transition temperature above room temperature, and wherein the polymer exhibits a lower glass transition temperature upon exposure to conditions encountered in vivo.

3. The optical fiber according to 1, wherein the polymer has a glass transition temperature above room temperature, and wherein the polymer exhibits a lower glass transition temperature than the temperature encountered in vivo.

4. The optical fiber according to any of 1 to 4, wherein the polymer comprises one or more of polyvinyl alcohol, poly(vinyl acetate), partially hydrolyzed poly(vinyl acetate), poly(vinylbutyral), partially hydrolyzed poly(vinylbutyral), poly(acrylate), acrylate copolymer, polyester, poly(acrylic acid), poly(ethylene oxide), ethylene oxide copolymer, poly(propylene oxide), propylene oxide copolymer, polyamide, poly(acrylamide), poly(N-vinyl pyrrolidone), and poly(methacrylic acid).

5. The optical fiber according to 4, wherein the polymer comprises polyvinyl alcohol.

6. The optical fiber according to any of 1 to 5, wherein the polymer is chemically or physically cross-linked.

7. The optical fiber according to any of 1 to 6, wherein said first stiffness is characterized by a tensile storage modulus of equal or greater than 1 GPa, and wherein said second stiffness is characterized by a tensile storage modulus of less than 500 MPa.

8. The optical fiber according to 7, wherein said first stiffness is characterized by a tensile storage modulus of greater than 2 GPa.

9. The optical fiber according to 7, wherein said first stiffness is characterized by a tensile storage modulus of greater than 4 GPa.

10. The optical fiber according to 7, wherein said first stiffness is characterized by a tensile storage modulus of greater than 6 GPa.

11. The optical fiber according to any of 7 to 10, wherein said second stiffness is characterized by a tensile storage modulus of less than 200 MPa.

12. The optical fiber according to 11, wherein said second stiffness is characterized by a tensile storage modulus of less than 100 MPa.

13. The optical fiber according to 11, wherein said second stiffness is characterized by a tensile storage modulus of less than 50 MPa.

14. The optical fiber according to 11, wherein said second stiffness is characterized by a tensile storage modulus of less than 10 MPa.

15. The optical fiber according to any of 1 to 14, wherein a propagation loss in the dry state is less than 1 dB/cm in a wavelength regime of 470-590 nm.

16. A stimulation device, comprising: the optical fiber according to any of 1 to 15 operatively connected to a light source such that a portion of the light from the light source can be conducted along the length of the fiber from a first end to a second end.

17. A method for producing an optical fiber according to any of 1 to 15, comprising the steps of: obtaining a solution comprising a largely amorphous polymer, spinning a fiber from the solution into a coagulation bath comprising a coagulant, removing the fiber from the bath; optionally orienting the fiber, crosslinking the polymer and annealing the fiber to produce the optical fiber.

18. A method for stimulating neurons, comprising the steps of: obtaining the stimulation device according to 16; inserting the second end of the optical fiber into a human or animal brain; and delivering light from the light source to the brain through the optical fiber.

While in accordance with the patent statutes the best mode and preferred embodiment have been set forth, the scope of the invention is not limited thereto, but rather by the scope of the attached claims.

What is claimed is:

1. A physiologically responsive mechanically adaptive optical fiber, comprising: a largely amorphous polymer, the optical fiber having a main body having a length between a first end and second end, wherein light can be transmitted along the length of the optical fiber, wherein the optical fiber has a first stiffness before exposure to conditions encountered in vivo, and upon exposure to conditions encountered in vivo the optical fiber exhibits a second stiffness lower than the first stiffness.

2. The optical fiber according to claim 1, wherein the polymer has a glass transition temperature above room temperature, and wherein the polymer exhibits a lower glass transition temperature upon exposure to conditions encountered in vivo.

3. The optical fiber according to claim 1, wherein the polymer has a glass transition temperature above room temperature, and wherein the polymer exhibits a lower glass transition temperature than the temperature encountered in vivo.

4. The optical fiber according to claim 1, wherein the polymer comprises one or more of polyvinyl alcohol, poly(vinyl acetate), partially hydrolyzed poly(vinyl acetate), poly(vinylbutyral), partially hydrolyzed poly(vinylbutyral), poly(acrylate), acrylate copolymer, polyester, poly(acrylic acid), poly(ethylene oxide), ethylene oxide copolymer, poly(propylene oxide), propylene oxide copolymer, polyamide, poly(acrylamide), poly(N-vinyl pyrrolidone), and poly(methacrylic acid).

5. The optical fiber according to claim 4, wherein the polymer comprises polyvinyl alcohol.

6. The optical fiber according to claim 1, wherein the polymer is chemically or physically cross-linked.

7. The optical fiber according to any of claims 1 to 6 claim 1, wherein said first stiffness is characterized by a tensile storage modulus of equal or greater than 1 GPa, and wherein said second stiffness is characterized by a tensile storage modulus of less than 500 MPa.

8. The optical fiber according to claim 7, wherein said first stiffness is characterized by a tensile storage modulus of greater than 2 GPa.

9. The optical fiber according to claim 7, wherein said first stiffness is characterized by a tensile storage modulus of greater than 4 GPa.

10. The optical fiber according to claim 7, wherein said first stiffness is characterized by a tensile storage modulus of greater than 6 GPa.

11. The optical fiber according to claim 7, wherein said second stiffness is characterized by a tensile storage modulus of less than 200 MPa.

12. The optical fiber according to claim 11, wherein said second stiffness is characterized by a tensile storage modulus of less than 100 MPa.

13. The optical fiber according to claim 11, wherein said second stiffness is characterized by a tensile storage modulus of less than 50 MPa.

14. The optical fiber according to claim 11, wherein said second stiffness is characterized by a tensile storage modulus of less than 10 MPa.

15. The optical fiber according to claim 1, wherein a propagation loss in the dry state is less than 1 dB/cm in a wavelength regime of 470-590 nm.

16. A stimulation device, comprising: the optical fiber according to claim 1, operatively connected to a light source such that a portion of the light from the light source can be conducted along the length of the optical fiber from a first end to a second end.

17. A method for stimulating neurons, comprising the steps of: obtaining the stimulation device according to claim 16; inserting the second end of the optical fiber into a human or animal brain; and delivering light from the light source to the brain through the optical fiber.

18. A method for producing an optical fiber according to claim 1, comprising the steps of: obtaining a solution comprising a largely amorphous polymer, spinning an optical fiber from the solution into a coagulation bath comprising a coagulant, removing the optical fiber from the bath; optionally orienting the optical fiber, crosslinking the polymer and annealing the optical fiber to produce the optical fiber.

* * * * *

UNITED STATES PATENT AND TRADEMARK OFFICE
CERTIFICATE OF CORRECTION

PATENT NO. : 10,481,323 B2
APPLICATION NO. : 15/112580
DATED : November 19, 2019
INVENTOR(S) : Christoph Weder et al.

Page 1 of 1

It is certified that error appears in the above-identified patent and that said Letters Patent is hereby corrected as shown below:

In the Claims

In Claim 7, please delete "any of claims 1 to 6"

Signed and Sealed this
Twenty-eighth Day of January, 2020

Andrei Iancu
*Director of the United States Patent and Trademark Office*